United States Patent
Bjerborn

(10) Patent No.: US 6,682,696 B1
(45) Date of Patent: Jan. 27, 2004

(54) METHOD OF STERILIZING A PACKAGE MATERIAL

(75) Inventor: Thomas Bjerborn, Lund (SE)

(73) Assignee: Tetra Laval Holding & Finance SA, Pully (CH)

( * ) Notice: Subject to any disclaimer, the term of this patent is extended or adjusted under 35 U.S.C. 154(b) by 0 days.

(21) Appl. No.: 09/284,050

(22) PCT Filed: Sep. 19, 1997

(86) PCT No.: PCT/SE97/01575

§ 371 (c)(1),
(2), (4) Date: Jul. 6, 1999

(87) PCT Pub. No.: WO98/16259

PCT Pub. Date: Apr. 23, 1998

(30) Foreign Application Priority Data

Oct. 14, 1996 (SE) .............................................. 9603735

(51) Int. Cl.⁷ ................................................. A61L 2/00
(52) U.S. Cl. ........................................... 422/28; 422/29
(58) Field of Search ............................. 422/4, 5, 28, 29

(56) References Cited

U.S. PATENT DOCUMENTS

| 3,891,779 A | * | 6/1975 | Robinson ..................... 422/28 |
| 3,893,832 A | * | 7/1975 | Perry et al. .................... 422/28 |
| 4,169,123 A | * | 9/1979 | Moore et al. .................. 422/28 |
| 4,225,556 A | * | 9/1980 | Lothman et al. .............. 422/28 |
| 4,396,582 A | * | 8/1983 | Kodera ........................ 422/28 |
| 4,512,951 A | * | 4/1985 | Koubek ....................... 422/28 |
| 4,537,749 A | * | 8/1985 | Hick ............................ 422/28 |
| 4,631,173 A | * | 12/1986 | Muller et al. ................. 422/28 |
| 4,731,222 A | * | 3/1988 | Kralovic et al. .............. 422/28 |
| 4,756,882 A | * | 7/1988 | Jacobs et al. ................. 422/28 |
| 4,797,255 A | * | 1/1989 | Hatanaka et al. ............. 422/28 |
| 5,114,671 A | * | 5/1992 | Olanders ...................... 34/640 |
| 5,417,681 A | * | 5/1995 | Miyake et al. .............. 604/410 |
| 5,674,450 A | * | 10/1997 | Lin et al. ....................... 422/29 |
| 5,958,486 A | * | 9/1999 | Ringdahl et al. ........... 426/126 |
| 6,333,061 B1 | * | 12/2001 | Vadhar ....................... 206/497 |
| 6,339,952 B1 | * | 1/2002 | Potter et al. ................ 426/549 |

FOREIGN PATENT DOCUMENTS

| EP | 0384535 | 8/1990 | |
| EP | 0481361 | 4/1992 | |
| JP | 60206859 A | * 10/1985 | ........... C08L/67/02 |
| JP | 07277318 A | * 10/1995 | ........... B65D/5/28 |
| JP | 09002458 A | * 1/1997 | ........... B65D/5/56 |
| JP | 09077051 A | * 3/1997 | ........... B65D/5/56 |

* cited by examiner

Primary Examiner—Robert J. Warden, Sr.
Assistant Examiner—S Balsis
(74) Attorney, Agent, or Firm—James Ray & Associates

(57) ABSTRACT

Containers which are ready to be filled or a package material having a plastic surface can be sterilized by hydrogen peroxide in a gaseous phase. The hydrogen peroxide is supplied to the previously heated plastic surface. The entire sterilization procedure is performed with the hydrogen peroxide in a gaseous phase.

3 Claims, No Drawings

METHOD OF STERILIZING A PACKAGE MATERIAL

The present invention refers to a method of sterilizing a package material. More precisely the invention refers to a method of sterilizing a package material having a plastic surface by means of hydrogen peroxide in gaseous phase being supplied to the previously heated plastic surface.

Sterile containers which are ready to be filled can be obtained in various ways. One method of sterilization implies that the plastic containers are sealed directly in connection with the manufacturing procedure, e.g. when blow moulded. Due to the collapse of the container at a subsequent lowering of the temperature the sealing in this case results in considerable problems. The container must therefore be stored at an elevated temperature since the volume of air enclosed in the container will decrease if the temperature is decreased. Such a storage is both cumbersome and costly. In order to avoid this, among other materials hydrogen peroxide is nowadays utilized in a liquid or gaseous phase, the inside of the containers then being sterilized.

Hydrogen peroxide is a very potent but not especially stable oxidant, and an advantage is that only plain water is formed as by-product. However, the half-life of hydrogen peroxide is very long, and the sterilizing agent has thus to be removed after it has been allowed to exert its effect.

Hydrogen peroxide is supposed to exert its antimicrobial activity through its powerful oxidizing effect by acting on components in the cytoplasmic membrane of the microorganisms. In the sterilizing procedure hydrogen peroxide is used as a water solution which is sprayed into a container. When the container is subsequently heated the hydrogen peroxide is gasified and can be ventilated away after having exerted its effect.

According to an alternative sterilizing procedure a container is in a first step subjected to hydrogen peroxide in gaseous phase, which is allowed to condensate on the inside of the container. By this procedure a homogeneous coating of hydrogen peroxide is obtained, which completely covers the package material. In a subsequent step the condensated gas is again gasified and is finally ventilated away. By this procedure an acceptable death rate of microorganisms for commercial sterilization can be achieved.

When for example plastic containers are sterilized these are in practice coated with a commercial standard solution, called "Oxonia Aktiv", which among other things contains hydrogen peroxide and peracetic acid. The solution is allowed to act for some minutes, and the containers are then rinsed with clean sterile water. Such a procedure is both complicated and time consuming.

A further problem is that with certain plastics in the package material, above all polyester, residues of hydrogen peroxide are obtained which are adsorbed on the inside of the container as a result of spraying, coating or condensation. They can afterwards have a negative influence on the filling material, for example by changing the colour. The authorities have established limit values which must not be exceeded for residues of hydrogen peroxide.

It is rather unusual to treat such a package material as a polyester aseptically since this type of material mostly is used for soft drinks and the like. However, there exists a great interest from the market for an aseptic bottle of polyethylene terephtalate (PET).

In order to minimize the risk of residual product formation the hydrogen peroxide can be ventilated away, e.g. at the elevated temperature or by sterile air being blown into the container. Such a procedure is costly and it would thus be desirable if shorter ventilation times could be used, which would result in a lower cost per container.

The purpose of the invention is to eliminate or reduce the drawbacks mentioned above which arise during a sterilization by means of hydrogen peroxide according to the state of the art.

In order to achieve this purpose the method according to the invention has obtained the characterizing features of claim 1.

A sterilizing process with a condensation of hydrogen peroxide comprises four phases of different time intervals: a heating phase, a gassing phase, a holding phase, and a ventilation phase.

During the heating phase the container is heated to a suitable temperature. The heating phase is not necessary. However, it reduces the amount of condensate which later on has to be ventilated away.

During the gassing phase gaseous hydrogen peroxide is injected into the previously heated container and over the surface which is to be exposed to the treatment, onto which the gas condensates, and a condensate in the form of droplets is formed. The gas used is a mixture of air and a gasified solution of hydrogen peroxide. The solution of hydrogen peroxide is supplied as a commercial grade which consists of about 65% water and about 35% hydrogen peroxide. However, other concentrations can of course be used in dependence of other parameters.

During the holding phase the condensate is allowed to exhibit its effect, and during the ventilation phase the container is ventilated, the condensate again being transformed into gaseous phase and removed from the container. In this connection hot air is used which has been pre-filtered and sterilized by means of filtration.

Experiments were performed with the purpose of achieving an equally effective sterilization as that which allows the hydrogen peroxide used to exert its effect in the form of a condensated gas. In these experiments the hydrogen peroxide was according to the invention allowed to remain in the gaseous phase during the entire sterilization procedure.

In comparison with the sterilization by means of condensation described above the method according to the invention implies briefly that the containers are sterilized with gasified hydrogen peroxide, the containers first being heated to a temperature which is higher than the dew point of the gas used. The containers are then blown to dryness with hot sterile air.

During the sterilization procedure the containers are thus for a certain period of time exposed to gaseous hydrogen peroxide of a specific temperature, dew point and flow rate. Apart from the hydrogen peroxide concentration these parameters are important in order to achieve an effective killing. In this connection the dew point is the temperature the gaseous hydrogen peroxide must be cooled to in order to obtain a condensation, a water solution of hydrogen peroxide being separated. This temperature is dependent on the hydrogen peroxide content in the gas. The dew point is adjusted to be used in an existing sterilizing equipment.

Preliminary experiments have shown that the amount of residual hydrogen peroxide per unit area varied after contact with different types of package material. Certain problems were obtained with polyester as a package material, and thus the experiments were concentrated on such a material by using bottles of polyethylene terephftalate. However, other types of containers which are ready to be filled were also studied.

EXAMPLE 1

Comparison Between Sterilizing Effects

A comparison was performed between the sterilizing effect achieved by means of gassing/condensation and that with gassing alone according to the invention. The efficiency with regard to killing microorganisms in the form of a logarithmic reduction was defined as the number of organisms in a reference sample minus the number of surviving organisms.

PET bottles were inoculated with spores of *Bacillus subtilis* NCA 7252, and after the respective sterilization treatment the results were statistically evaluated with a conventional procedure (based on the method with "Most Probable Number") which is well known to the man skilled in the art.

The containers to be subjected to gassing/condensation or gassing alone according to the invention, respectively, received the same treatment during the gassing phase and the holding phase, which treatment by way of earlier experiments had been found to be optimal.

Thus, in the sterilization procedure a gassing phase of 3 sec was used with gaseous hydrogen peroxide, the gas having a temperature of 90° C., a dew point of 65° C., and a flow rate of 40 kg/h. The length of the holding phase was 1 sec.

Those containers which should be subjected to gassing/condensation were during the heating phase heated to 50–55° C., and the containers were ventilated for 10 sec with sterile air of 70° C. having a flow rate of 40 gk/h. During the gassing/condensation the ventilation time was adjusted in such a way that all visible condensate had evaporated. Those containers which had been subjected to gassing alone according to the invention were during the heating phase subjected to a temperature of 70–80° C., and during the ventilation phase the containers were fluxed for 2 sec with sterile air of 80° C. at a flow rate of 60 gk/h. The results indicated that a sufficient killing effect was achieved in the form of a logarithmic reduction of at least log 5 ($10^5$) with both sterilizing methods.

EXAMPLE 2

Comparison Between Evolved Residual Amounts

Experiments were performed in order to study if any residues were obtained in PET containers sterilized according to the invention. At the same time a comparison was performed with polyethylene (PE) bottles.

Bottles of PET and PE were subjected to the same sterilization treatment as in Example 1 apart from that the time after the filling of the bottles, the storage time, was varied and that the ventilation time after the two sterilization procedures was 2 sec. Residual hydrogen peroxide in each container was measured by means by a vial HP-10 (Chemetrics, 90298-31) according to the instructions of the manufacturer. The results obtained are shown in Table 1.

TABLE 1

Residual hydrogen peroxide (ppm) after sterilization (2 sec ventilation time).

| | Material | | | |
| --- | --- | --- | --- | --- |
| | PE | PET | | |
| Storage time (min) | 5 | 10 | 30 | 90 |
| Gassing | 0.5 | 3 | 3 | 3 |
| Condensation | — | 10 | >10 | — |

The results show that no significant residual hydrogen peroxide was obtained with polyethylene. It is also possible to reduce residual hydrogen peroxide to an acceptable level in a PET container which has been subjected to gassing according to the invention and then ventilated for such a short ventilation time as 2 sec. About 3 times more residuals are obtained in a PET bottle sterilized by means of condensation. This tendency is maintained even with such a short ventilation time as 15 sec (Table 2).

TABLE 2

Residual hydrogen peroxide (ppm) after sterilization (15 sec ventilation time).

| | Material | |
| --- | --- | --- |
| | PE | PET |
| Storage time (min) | 5 | 30 | 250 |
| Gassing | 0 | 0.3 | 0.1 |
| Condensation | 0 | 0.8 | 0.2 |

Thus, when gassing according to the invention low residual amounts were obtained of the sterilization medium hydrogen peroxide used together with an effective killing. This reduction in the number of microorganisms can also be increased by increasing the dew point (the gas concentration) or by prolonging the gassing phase. However, if the dew point is increased too much the residual amounts will increase with the gassing procedure according to the invention.

The sterilization method according to the invention is preferably intended to be used for sterilizing containers which are ready to be filled and/or for a package material having a plastic surface which can comprise a polyester, e.g. polyethylene terephtalate. However, the method is not limited to containers which are ready to be filled. On the contrary, it is an advantage if a container is sterilized as a "preform", i.e. before it—for example by means of blow moulding—has obtained its final form which has a difficult geometry from a sterilizing point of view. In this case smaller residual amounts per unit area will be obtained in the completed container. The package material in the form of a sheet or a web can thus in the same way as a container which is ready to be filled be subjected to the above mentioned four phases, heating phase, gassing phase, holding phase, and ventilation phase, the sterilization being effected by means of the method according to the invention. In this connection the package material may well be treated continuously.

What is claimed is:

1. Method of sterilizing package material having a plastic surface by hydrogen peroxide in a gaseous phase being supplied to the previously heated plastic surface, wherein the plastic surface, comprising a polyethylene terephthalate, is heated to a temperature which is higher than the dew point for the hydrogen peroxide in gaseous phase, wherein the dew point is the temperature that the gaseous hydrogen peroxide must be cooled to in order to obtain a condensation, and the entire sterilization procedure is performed with the hydrogen peroxide in a gaseous phase such that any residual hydrogen peroxide remaining on said plastic surface is 3 ppm or less after two seconds of ventilation time with the application of sterile air at 80° C. having a flow rate of 60 gk/h.

2. Method as claimed in claim 1, characterized in that the package material having a plastic surface is sterilized before the package material is shaped into a container such that said sterilized surface forms an inner surface of said container.

3. Method as claimed in claim 2, characterized in that the package material having a plastic surface is a web of material which is continuously fed during said sterilization procedure.

* * * * *